United States Patent
Haas et al.

(10) Patent No.: US 9,069,999 B1
(45) Date of Patent: *Jun. 30, 2015

(54) VARIABLE FAN FOR PORTABLE EXPLOSIVE OR DRUG DETECTION SYSTEM

(71) Applicants: Jeffrey Haas, San Ramon, CA (US); Douglas Haas, Lancaster, CA (US)

(72) Inventors: Jeffrey Haas, San Ramon, CA (US); Douglas Haas, Lancaster, CA (US)

(73) Assignee: CHEM SPECTRA, INC., Lancaster, CA (US)

( * ) Notice: Subject to any disclaimer, the term of this patent is extended or adjusted under 35 U.S.C. 154(b) by 102 days.

This patent is subject to a terminal disclaimer.

(21) Appl. No.: 13/716,074

(22) Filed: Dec. 14, 2012

Related U.S. Application Data

(63) Continuation of application No. 12/699,536, filed on Feb. 3, 2010, now Pat. No. 8,363,887.

(51) Int. Cl.
*G06K 9/00* (2006.01)
*G01N 35/00* (2006.01)
*G01N 33/53* (2006.01)

(52) U.S. Cl.
CPC ........................................ *G06K 9/00* (2013.01)

(58) Field of Classification Search
None
See application file for complete search history.

(56) References Cited

U.S. PATENT DOCUMENTS

| | | | |
|---|---|---|---|
| 5,841,884 A * | 11/1998 | Yamamoto | 382/110 |
| 6,518,068 B1 * | 2/2003 | Gambini et al. | 436/50 |
| 2003/0044318 A1 * | 3/2003 | Olson | 422/58 |
| 2003/0166298 A1 * | 9/2003 | Suslick | 436/169 |
| 2005/0101027 A1 * | 5/2005 | Haas | 436/109 |
| 2007/0177032 A1 * | 8/2007 | Wong | 348/223.1 |
| 2007/0298513 A1 * | 12/2007 | Starzl et al. | 436/164 |
| 2007/0299309 A1 * | 12/2007 | Seibel et al. | 600/117 |
| 2008/0302237 A1 * | 12/2008 | Grate et al. | 95/18 |
| 2009/0029453 A1 * | 1/2009 | Lambotte et al. | 435/288.7 |
| 2009/0062134 A1 * | 3/2009 | Linton et al. | 506/7 |

* cited by examiner

*Primary Examiner* — Bhavesh Mehta
*Assistant Examiner* — David F Dunphy
(74) *Attorney, Agent, or Firm* — Tran & Associates

(57) ABSTRACT

Systems and methods are disclosed to automatically detect the presence of a substance on a test swipe by capturing a background image of the test swipe; applying one or more test chemicals to a test swipe; adjusting the temperature of the test swipe to a predetermined temperature range; controlling a variable speed fan to avoid fogging the camera's lens; capturing an in-situ image of the test swipe after the application of chemical at the predetermined temperature range; subtracting the background image from the in-situ image; generating a difference value from the two images; and searching a known database to identify the substance.

21 Claims, 12 Drawing Sheets

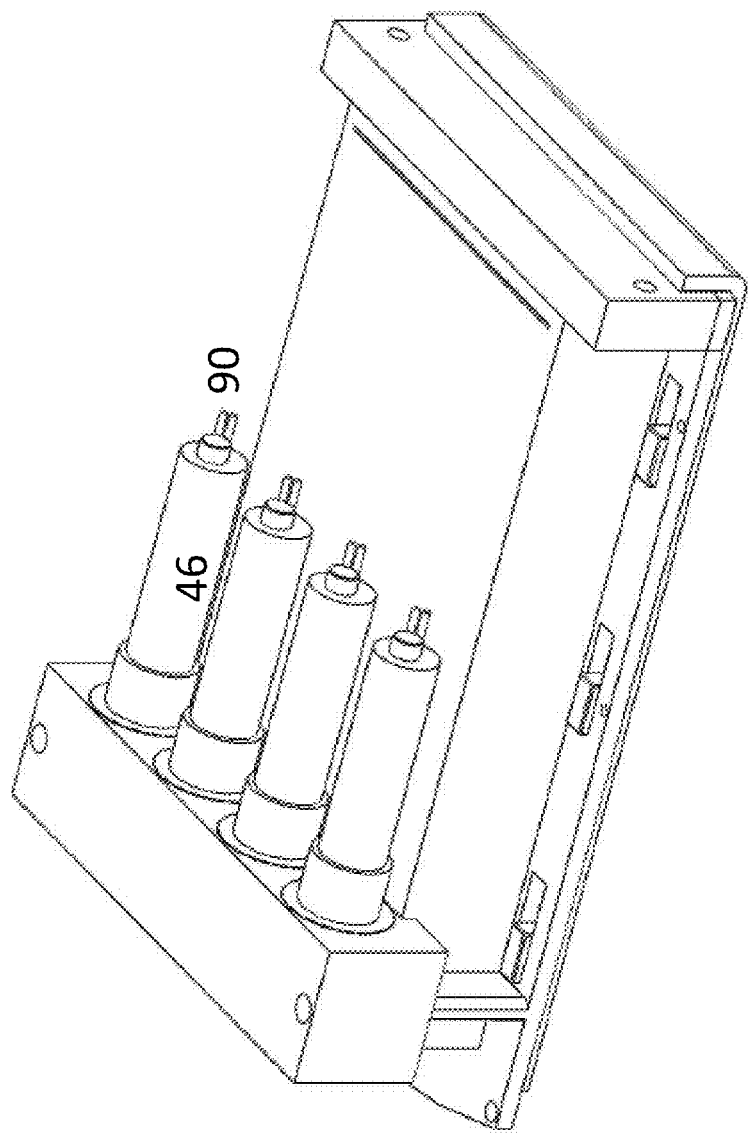

Initialization – train camera to detect outline of test swipe pad; initialize clear image threshold Deposit chemicals on test swipe Check camera image for blurredness caused by fogging If the blurredness exceeds a threshold, increase fan speed If blurredness equals the clear image threshold, turn off fan

FIG. 5C

VARIABLE FAN FOR PORTABLE EXPLOSIVE OR DRUG DETECTION SYSTEM

This case is a continuation of application Ser. No. 12/699,536 filed 3 Feb. 2010, the content of which is incorporated by reference.

BACKGROUND

This invention relates to systems for the detection of explosives and other controlled substances such as drugs or narcotics as well as other chemicals used in clandestine activities.

Recent terror attacks have changed the dynamics of the explosive detection systems across the globe. Terrorists, acting singly or in concert, instill immense fear and apprehension in civilians and governments alike with their technical knowledge about explosives. In parallel, the world has experienced an increase in the transportation of contraband substances such as drugs or narcotics.

With advances in explosives technology, such as the advent of the plastic explosives, which can be disguised as common items, it is becoming increasingly difficult to detect these substances. The problems that must be overcome in the detection of these substances as well as others, include low vapor pressure of the particular vapors escaping from the particular substance, the search time and the throughput of the various systems, the low concentration of vapor or particulate emissions from the particular substance, isolation of the particular substance with a high degree of reliability, and maintaining the integrity of the systems environment.

Various techniques for detecting substances such as explosives and drugs or narcotics have been developed, ranging from explosives/drug sniffing dogs to highly sophisticated vapor detection devices. Machine detection of the aforementioned substances can be accomplished through non-vapor detection or vapor detection. Non-vapor detection methods include x-ray detection, gamma-ray detection, neutron activation detection and nuclear magnetic resonance detection. These methods of detection are more applicable to the detection of the various substances when the substances are concealed and are carried or associated with non-living items such as baggage as these techniques might pose a threat to living items. Vapor detection methods include electron capture detection, gas chromatography detection, mass spectroscopy detection, plasma chromatography detection, bio-sensor detection and laser photo-acoustic detection. These methods of detection are more applicable to the detection of substances that are concealed and associated with living specimens.

Conventional systems tend to be large and immobile. Further, current systems can require users to manually apply toxic chemicals as testing agents. As a result, conventional systems are not mobile and hard to use. Hence, their adoption for field use has been limited.

SUMMARY

In one aspect, systems and methods are disclosed to automatically detect the presence of a substance on a test swipe by capturing a background image of the test swipe; applying one or more test chemicals to a test swipe; adjusting the temperature of the test swipe to a predetermined temperature range; controlling a variable speed fan to avoid fogging the camera's lens; capturing an in-situ image of the test swipe after the application of chemical at the predetermined temperature range; subtracting the background image from the in-situ image; generating a difference value from the two images; and searching a known database to identify the substance.

Implementations of the above aspect may also include one or more of the following. The fog determination is based on the degree of image blurredness. Since a blurred image results from a fog, the method estimates the degree of image blurredness for fog determination. Based on the fog level, the method increases the fan speed to counter the fog until the image clears up. Once this is achieved, the fan is turned off or reduced to a minimal level until fogging occurs again, in which case the fan speed is increased. In one implementation, the fan speed can be varied by changing the pulse width if the motor is controlled by PWM. Alternatively, the fan motor speed can be adjusted by varying the voltage input provided to the fan motor. To estimate the degree of image blurredness, the method performs differential processing (or differential calculation) for each pixel on an entire image to calculate the edge amount of brightness. Based on the edge amount, the method estimates the degree of image blurredness. Since a blurred image indicates a small edge amount as a whole, it is possible to estimate the degree of image blurredness based on the edge amount.

In another aspect, a method to analyze a swiped sample to identify a chemical composition, includes clamping a test swipe under a camera and above a heater, the test swipe having a base; a chemically treated swipe containing the swiped sample positioned above the base; and a tab attached to one side of the base; automatically applying a series of chemical solution agents by piezoelectric units or pumps onto the swiped sample without dripping so that the device may be held at any angle of position or orientation; heating the swiped sample to one or more predetermined temperatures at a controlled rate and hold times to optimize and accelerate the chemical reactions; controlling a variable speed fan to avoid fogging the camera's lens; capturing one or more images of the chemical reaction; sending the images to the a display screen for operator observation; and analyzing the images to identify the chemical composition based on a chemical reaction and sequence of occurrence and database.

In yet another aspect, a portable handheld chemical analytical apparatus to analyze a test swipe for chemicals such as household, drug, and clandestine, and explosive chemicals is disclosed. The apparatus includes a heater to warm the test swipe to a predetermined temperature; a clamp to secure the test swipe to the heater; dispensing one or more chemicals by piezoelectric units or pumps onto the test swipe; a variable speed fan to circulate chemical vapors rising from the test swipe and to avoid fogging the lens; and a camera to capture an image of the test swipe for analysis.

In another aspect, a method to analyze a swiped sample to identify a chemical composition, includes automatically applying a series of chemical solution agents by piezoelectric units or pumps onto the swiped sample; heating the swiped sample to one or more predetermined temperatures at a controlled rate to accelerate and optimize the chemical reactions or a series of chemical reactions reproducibly; controlling a variable speed fan to avoid fogging the camera's lens; capturing one or more images of the chemical reaction; sending the images to the a display screen for operator observation; and analyzing the images electronically to identify the chemical composition in an unbiased fashion based on a chemical reaction database.

Advantages of the system may include one or more of the following. The variable fan reduces inaccurate readings due to blurredness caused by fogging. The system significantly enhances the possibility of accurately and quickly screening personnel, equipment, and materials at security checkpoints, military operations, law enforcement, or other screening scenarios, and for detecting trace explosive materials, drugs, and chemical compositions night or day, and in very high humidity and bad-weather conditions. The system allows users to precisely and quickly detect different explosive, drug, or chemical agents.

The system operates in a real-time fashion. It automatically dispenses a precise volume of chemical solutions over time when requested. The system optionally allows users to manually control the sequence of the piezoelectric or pumping process. The system provides users with piezoelectric or pump controls for dispensing chemical solutions. Through the built-in heater, the system automatically heats up the swiped sample to predetermined temperatures over specific time parameters using an automatic ramped heating feedback control. The system automatically and continually performs self-check and monitors fluid levels, temperature and time. The system automatically chronologically stores data and arranges according to positive results versus negative results. The system automatically tells the operator to remove the analyzed swipe. The system delivers a unique sequence of precise chemical volumes under time, heat, and vapor parameters. The system has detachable and expendable chemical(s) in cartridge form for ease of replacement. The system uses a high-resolution digital camera for data collection and unbiased automated analysis.

By use of a wired or wireless transceiver, detected information can be easily transmitted to anywhere in the world. By replacing disposable swipes and disposable chemical test reservoirs, the system can detect a wide range of explosives, clandestine material, drugs, and household products used to manufacture explosives. By allowing the user to swipe test materials and running computerized diagnostics, the user can easily and effectively change the system to meet what is considered to be the threat at that time. By having all components under program control and by arranging for a known input to the system such as a controlled injection of target material, the system can perform self-calibration and self-diagnostics.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which:

FIG. 1 shows an exemplary portable chemical detection device, while

FIG. 4C shows an exemplary perspective view of a micro-pump or piezoelectric array.

FIG. 5C shows an exemplary pseudo-code to perform anti-fogging using a variable speed fan.

DESCRIPTION

The following detailed description of the invention is provided to aid those skilled in the art in practicing the present invention. Even so, the following detailed description of the invention should not be construed to unduly limit the present invention, as modifications and variations in the embodiments herein discussed may be made by those of ordinary skill in the art without departing from the spirit or scope of the present inventive discovery.

Figure 1:
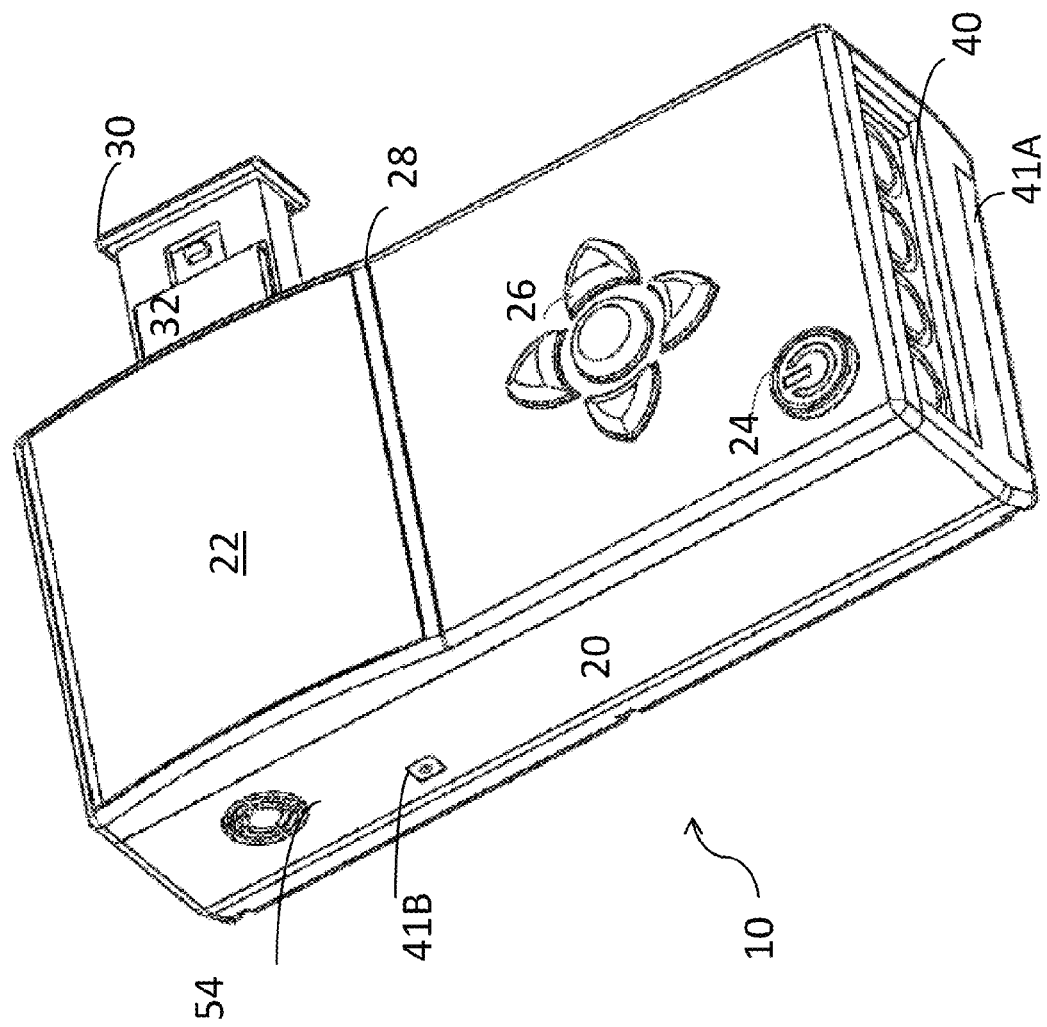

FIG. 1 shows an exemplary portable chemical detection device 10. The device 10 has a housing 20 that supports a display 22 and input devices such as an on-off button 24 and navigation/selection buttons 26. In one embodiment, the system has six buttons. The first button is the On/Off button. This button allows user to turn the unit on or off. The remaining five buttons (Left, Right, Down, Up, and Enter) allows user to interact with a Graphical User Interface (GUI) of the system. The GUI is flexible, efficient and user friendly.

The device 10 also has an input/output port 28 such as a USB port or Firewire port to communicate with a remote computer, and AC power port, among others. In one embodiment, the I/O port 28 is a weather proof PC interface. The PC interface can set up operation parameters and recover analyzed data. In another embodiment, the I/O port 28 can include a flash memory card interface.

The device 10 also includes two ports 30 and 40 to receive user replaceable media and chemical. The device 10 also includes a port 41A to receive user replaceable DC battery cartridge. Port 30 receives a test swipe of FIGS. 1A and 1B. The port 40 receives a chemical cartridge, which can house one or more chemical containers. An electronic controller 58 (shown in FIGS. 2A AND 2B) receives inputs from the buttons or keys and controls the display 22 and other electronics in the device 10. The system can work with different power sources including battery port 41A port and/or a DC input port 41B such as a car jack or an AC/DC adaptor.

The system of FIG. 1 is preferably a hand-held unit, which can most preferably be operated easily in real time by one operator. Moreover, the operation of such detectors should preferably be simple so that non-technical persons can operate the instrument properly, efficiently, and easily.

Figure 2:
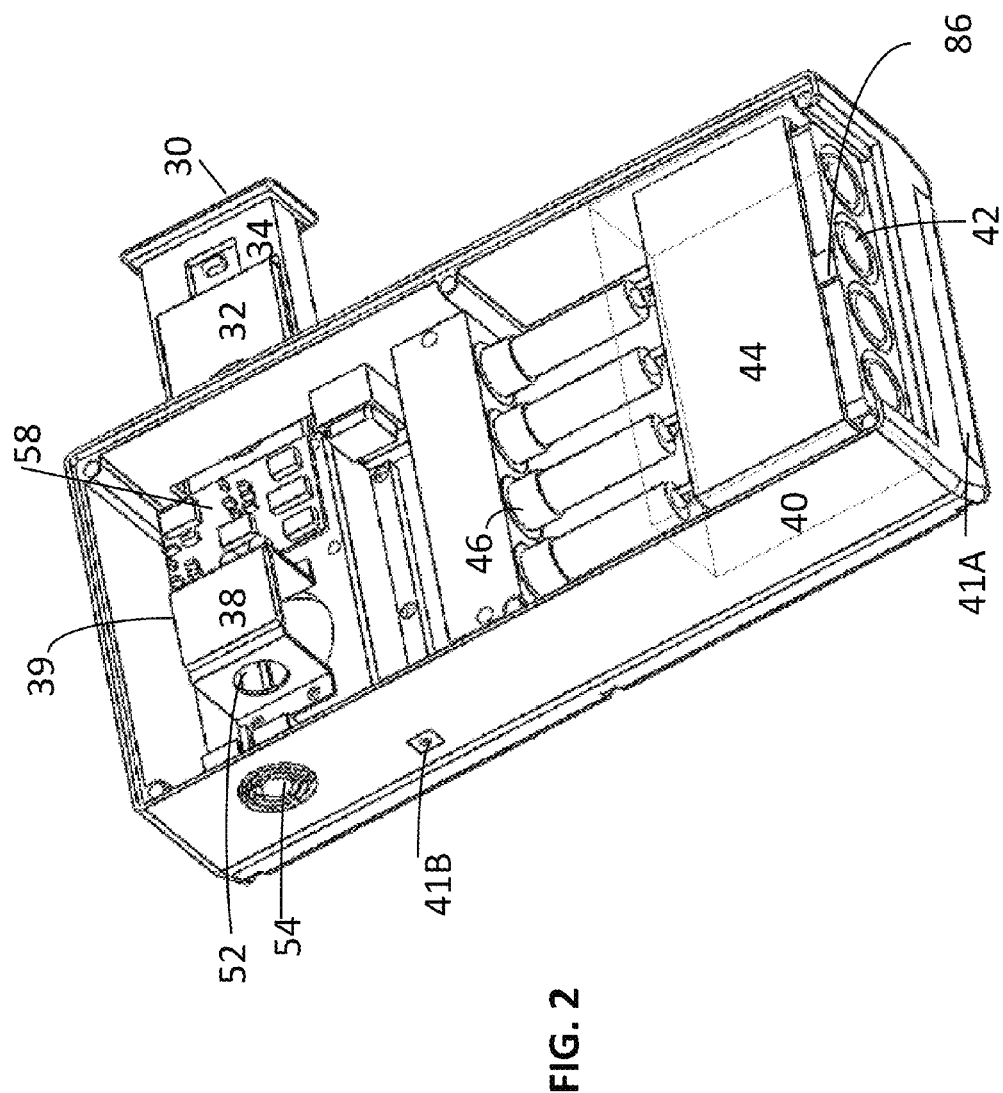
FIG. 2 shows in more details major components of the device.

FIG. 2 shows a perspective top view that show in more details major components of the device 10. In the embodiment of FIG. 2, a plurality of chemical containers or reservoirs 42 are mounted in a disposable cartridge 44 that is inserted into the unit 10. The reservoirs 42 are punctured via safety needles with a side port and the chemicals are automatically or manually pumped from the reservoirs 42 by one or more piezoelectric units or micro-pumps 46. The chemicals are delivered through one or more short length and narrow ID delivery tubes connected to the outputs of the piezoelectric units or micro-pumps 46 to the test swipe during testing.

Figure 5A:
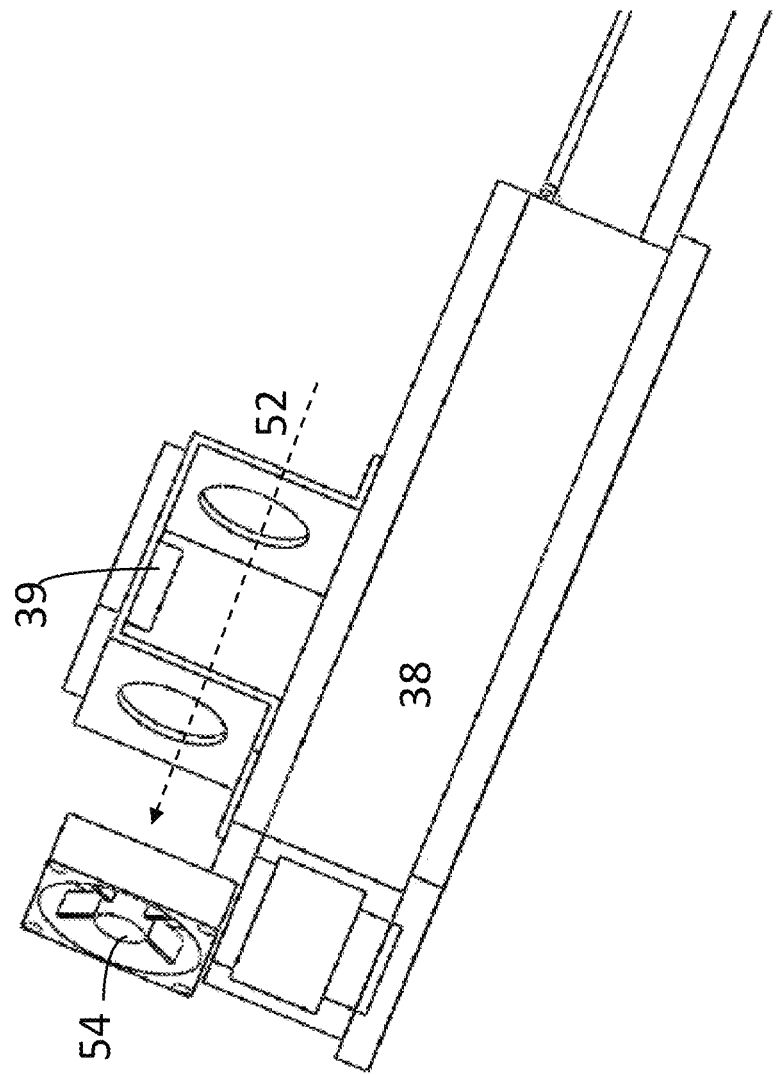
FIG. 5A shows an exemplary perspective view of a camera in a test chamber.

To test a contaminate collection swipe, a user opens the port 30 and places a test swipe therein. The swipe holder 34 moves along sliding rails 66 (FIG. 3) as the user closes the port 30. The swipe holder 34 stops at a predetermined location to place the test swipe under a test chamber 38. The test chamber 38 includes a chamber with two openings 52 that face a variable speed fan 54 to draw air across the test swipe while under test. The test chamber also includes a heating element (not shown) connected to a PID loop that can warm up the test swipe to multiple predetermined temperature settings during test. The test chamber also contains a camera 39 (FIGS. 2B and 5A).

Figure 3:
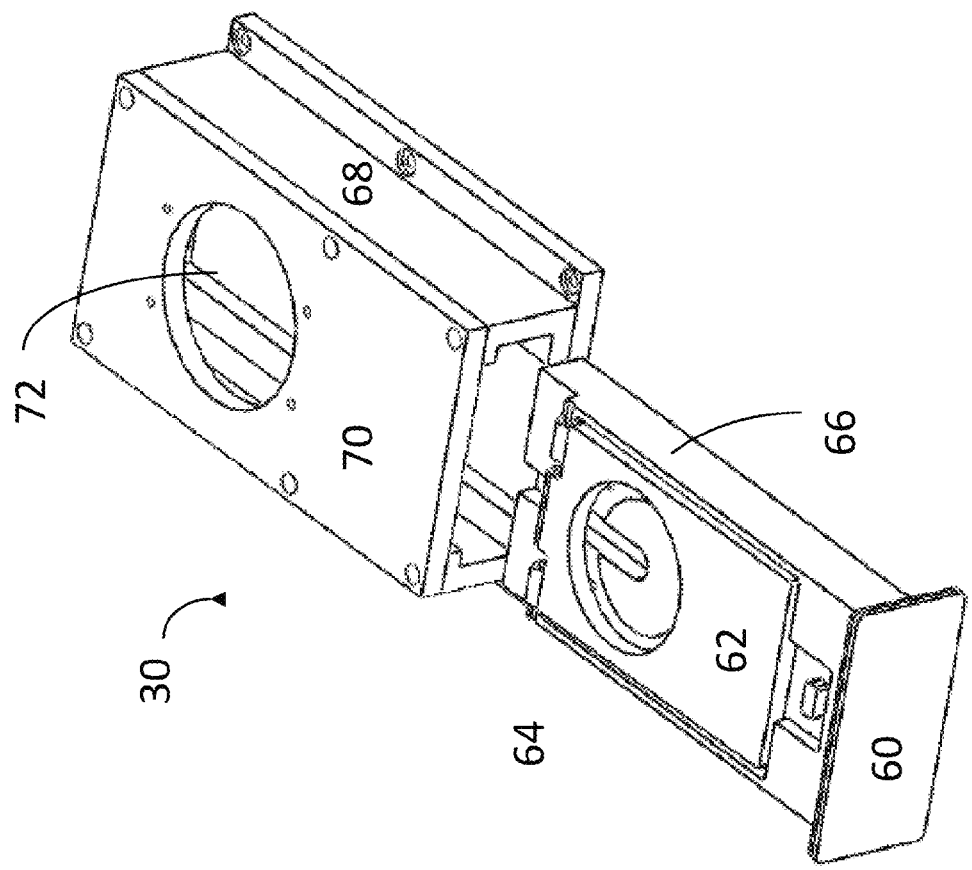
FIG. 3 shows in more details a swipe receiving port.

FIG. 3 shows in more detail port 30 that receives the test swipe in the swipe holder 64. The swipe holder 64 includes a door 60 by which a user can press against to open or close the port 30. The swipe holder 64 also includes an open face press-fit clamp 62 that secures the swipe against a heating element (not shown) under the swipe upon closure. The swipe holder 64 is attached to rails 66 that slide within rails 68 to enable the swipe holder 64 carrying the test swab of FIG. 1A or 1B to move in and out of the device 10. An enclosure for the swipe holder 64 is formed by positioning a lid 70 with an opening 72 between the sliding rails 68. The opening 72 allows movable tubes from the piezoelectric units or micropumps 46 to dispense test chemicals onto the swipe. The opening 72 also allows a camera 39 (FIG. 5A) to capture images of the test results for automatic real-time analysis of the test. A white-light source such as one or more LEDs are positioned near the camera can be turned on to provide lighting if needed and turned off when not used to conserve power. In one embodiment, the camera output is shown on the display 22 so that the user or operator can visually determine the test result(s) while the automated determination is in progress. The opening 72 also allows a variable speed fan 54 to gently move vapor away from the camera lens to avoid fogging the lens (anti-fogging).

Figure 4A:
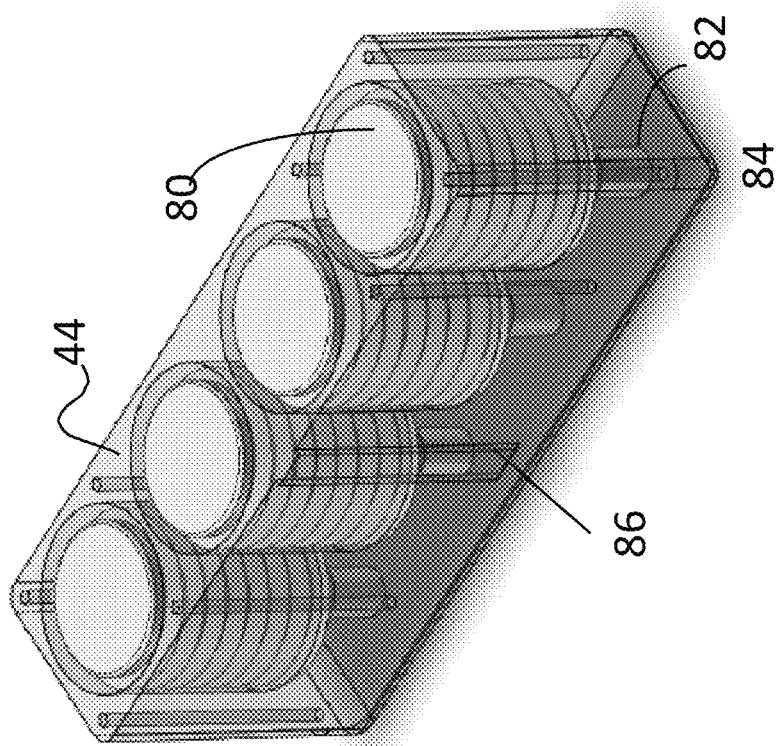
FIG. 4A shows a perspective view of a chemical supply cartridge.

FIG. 4A shows a perspective view of a disposable chemical supply cartridge 44 that can be inserted into the port 40. The disposable cartridge 44 contains one or more reservoirs 80, each having an inlet 82 that can be punctured and is re-sealable so that the chemical in each reservoir 80 can be accessed by a tip or safety needle 84. The disposable cartridge 44 also has a key 86 cooperating with a recess 87 (FIG. 4B) to ensure that the cartridge 44 can only be inserted in a predetermined orientation.

Figure 4B:
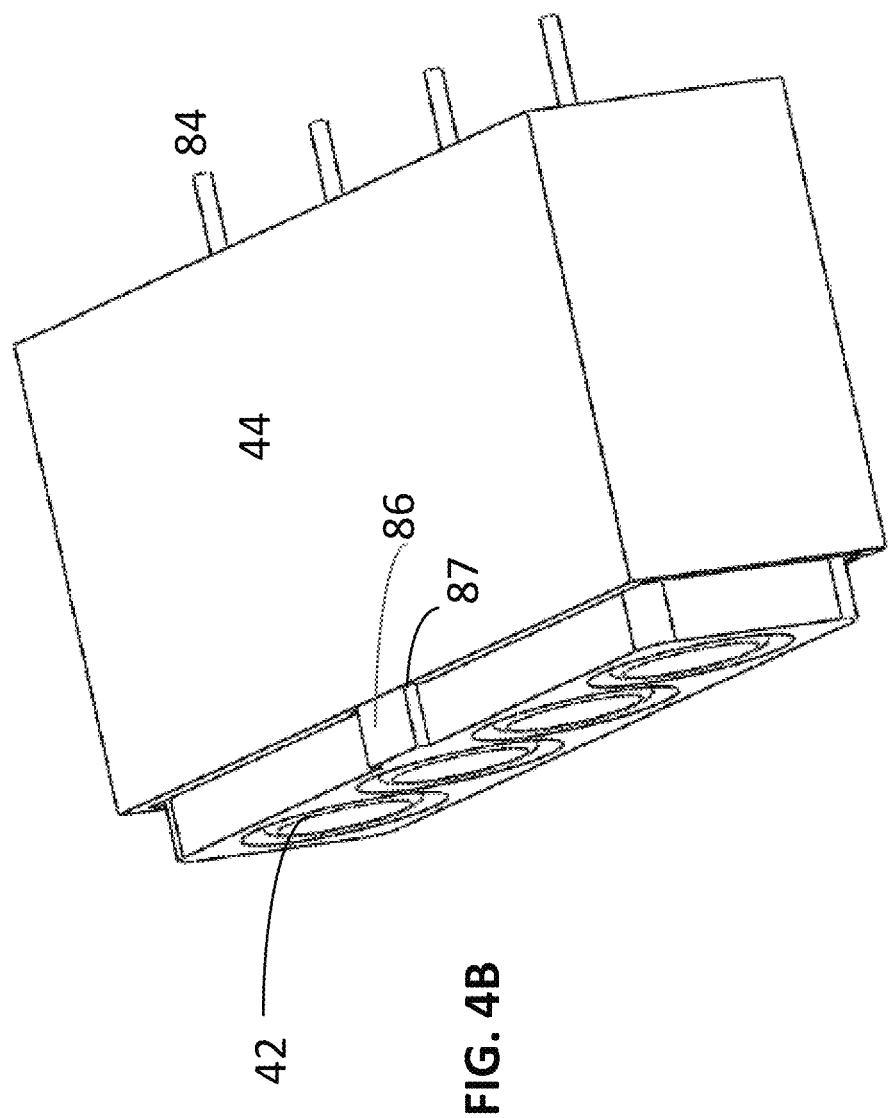
FIG. 4B shows an exemplary perspective top view of a pump assembly.

FIG. 4B shows an exemplary cartridge 44. The needles 84 provide chemicals through short length, narrow gauge tubes (not shown) to their respective inputs 90 (FIG. 4C) at the piezoelectric units or micro-pumps 46.

FIG. 4C shows an exemplary perspective view of a piezo-electric or micro-pump array. As shown therein, a plurality of piezoelectric units or micro-pumps 46 are provided to apply a series of respective chemicals from the array of reservoirs 80. Each piezoelectric unit or micro-pump has an inlet 90 that is connected to the needles that may or may not include safety tips and that are inserted into each reservoir 80 when the user inserts the cartridge 44 into the device 10. Another set of tubes are connected to the outputs of the piezoelectric units or micro-pumps 46 to deliver the chemicals in precise volume, sequence and timing as controlled by the processing electronic controller 58.

Figure 5B:
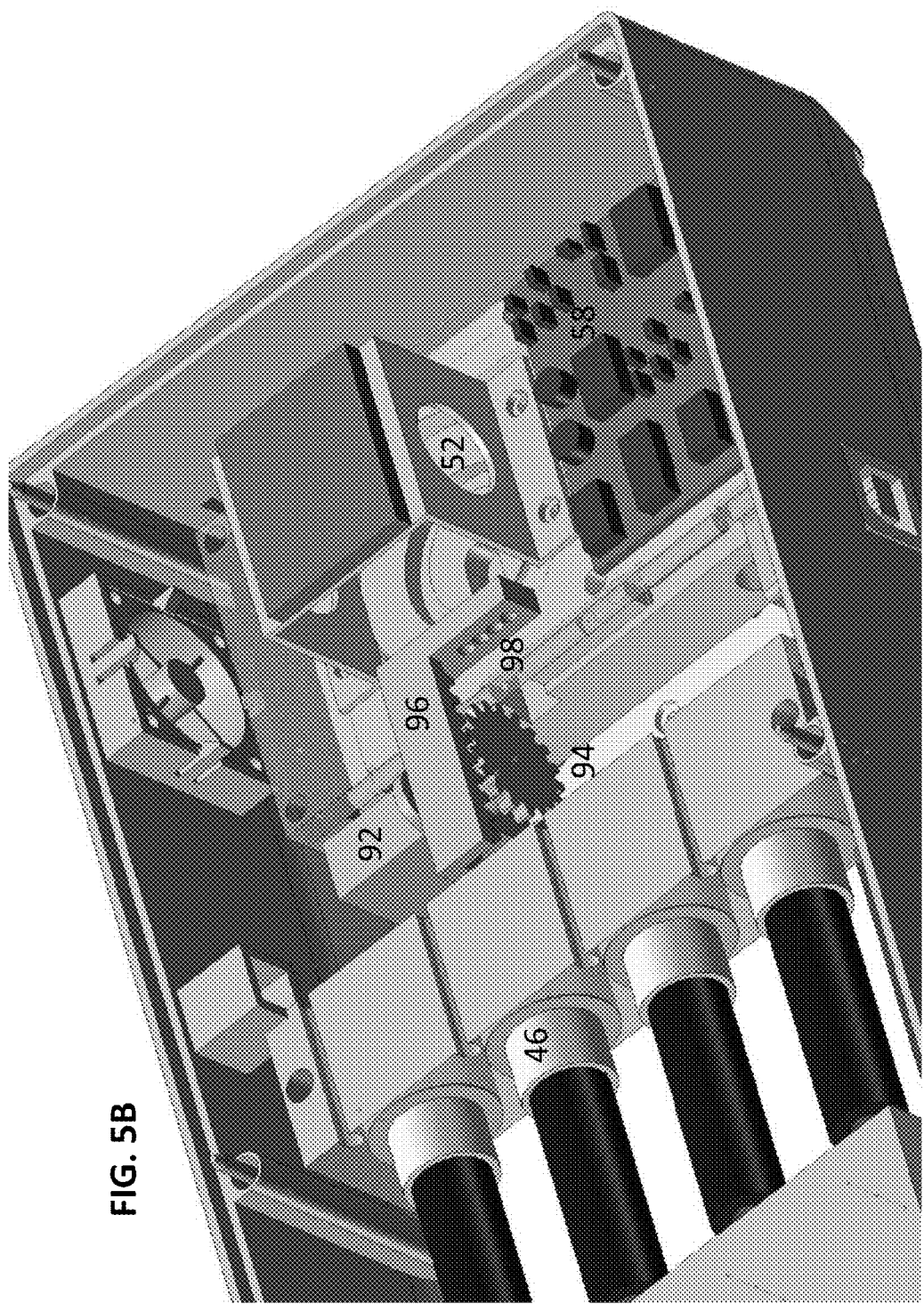
FIG. 5B shows an exemplary perspective view of tubing and camera actuator in the test chamber.

FIGS. 5A and 5B show an exemplary perspective view of a camera 39 in conjunction with the test chamber 38. The chamber 38 includes a motor 92 driving a gear 94. The gear 94 cooperates with a moveable arm 96 that moves test tubing fixture 98 back and forth over the test swab or swipe during testing. The test tubing fixture 96 moves very closely to the swipe for chemical deposit onto the swipe when the device 10 is held in any orientation. The arm 96 includes a plurality of openings that receive a plurality of tubes from the output of the piezoelectric units or micro-pumps 46. The arm 96 also moves the fixture 98 out of the way for the camera 39 to capture changes on the test swipe during testing. The camera images are then analyzed, and the result can then be displayed on the display 22. In one embodiment, the camera 39 can capture raw images with 65,536 colors. The camera is protected with an anti-fog feature using the adjustable speed fan 54. The image data can be shown continuously throughout the entire process on a flip-up display 22 with high fidelity. In one embodiment, the system provides a software JPEG (or alternatively bitmap) encoder and decoder for storing and viewing previous results and images. The system also includes white light LEDs (not shown) located within the test chamber 38 that provides even, shadow free, and uniform lighting during camera 39's operation with a programmable white light intensity. The LEDs minimize shadows in the camera viewing area.

The swipe holder 34 moves along rugged sliding rails 66 when the user closes the port 30 to place the test swipe of FIG. 1A or 1B under the test chamber 38. The test chamber 38 includes a chamber with two openings 52 that face the fan 54 to draw air across the test swipe while under test. The test chamber also includes a heating element 56 that can warm up the test swipe to a predetermined temperature during test.

FIG. 5C shows an exemplary pseudo-code of a method to provide a variable fan to provide anti-fogging capability during testing. The fog determination is based on the degree of image blurredness. Since a blurred image results from a fog, the method estimates the degree of image blurredness for fog determination. Based on the fog level, the method increases the fan speed to counter the fog until the image clears up. Once this is achieved, the fan is turned off or reduced to a minimal level until fogging occurs again, in which case the fan speed is increased. In one implementation, the fan speed can be varied by changing the pulse width if the motor is controlled by PWM. Alternatively, the fan motor speed can be adjusted by varying the voltage input provided to the fan motor.

Figure 6:
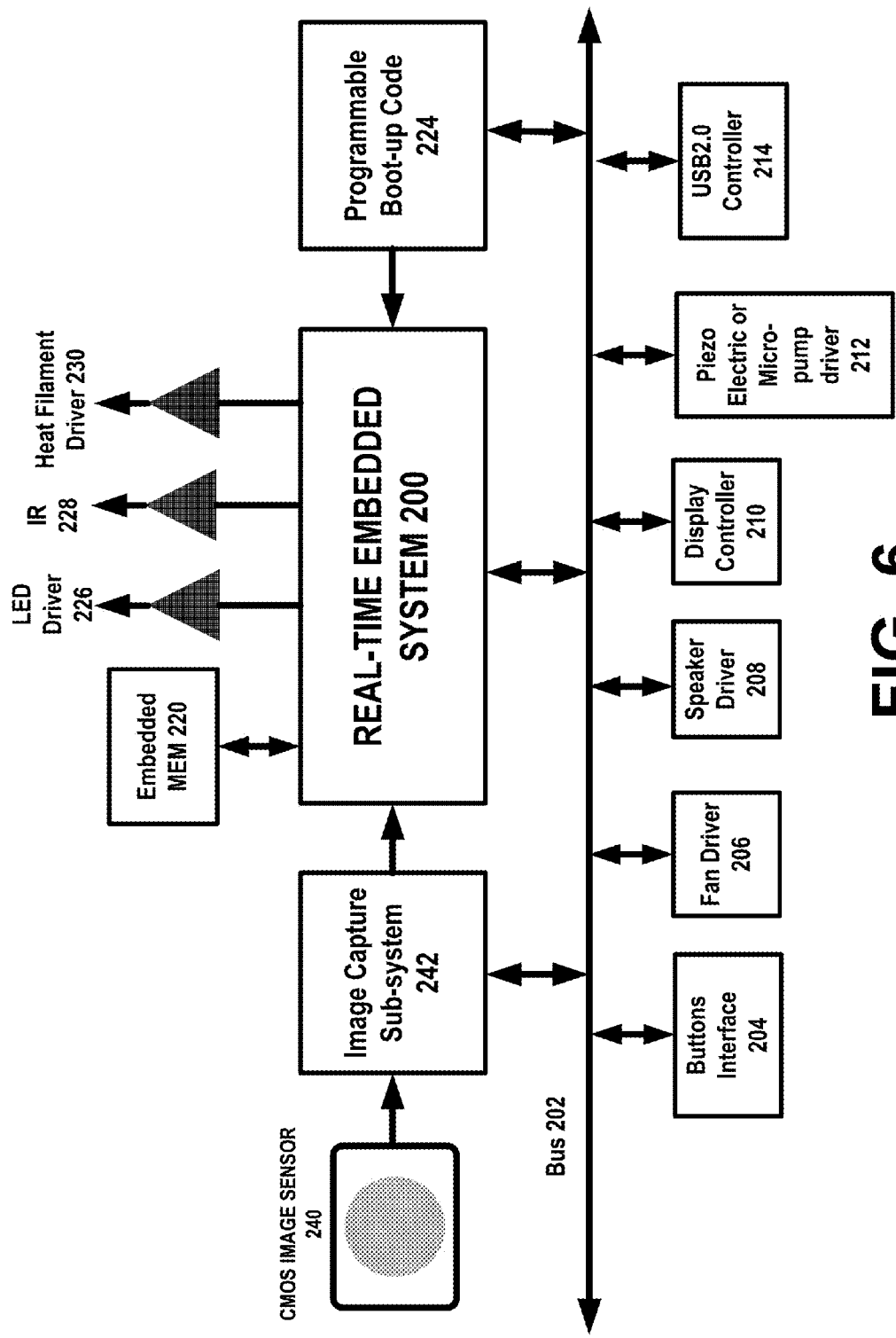
FIG. 6 shows an exemplary block diagram of processing electronics for the system of FIG. 2A.

To estimate the degree of image blurredness, the method performs differential processing (or differential calculation) for each pixel on an entire image to calculate the edge amount of brightness. Based on the edge amount, the method estimates the degree of image blurredness. Since a blurred image indicates a small edge amount as a whole, it is possible to estimate the degree of image blurredness based on the edge amount. As shown in FIG. 5C, the code to provide anti-fogging is as follows:

Initialization—train camera to detect outline of test swipe pad; initialize clear image threshold
Deposit chemicals on test swipe
Check camera image for blurredness caused by fogging
If the blurredness exceeds a threshold, increase fan speed
If blurredness equals the clear image threshold, turn off fan FIG. 6 shows an exemplary block diagram of processing electronics for the system of FIG. 2A. A processor 200 controls all tasks done by the system. The processor 200 communicates over a bus 202 to various devices, including buttons interface 204, fan driver 206, speaker driver 208, display controller 210, piezoelectric unit or micro-pump driver 212, and USB controller 214. The processor 200 also communicates with embedded memory 220 and a programmable ROM 224 that contains boot code as well as application code. The processor 200 also drives buffers 226, 228 and 230 which controls the LED(s), infrared sensor that informs the operator if a swipe has been loaded into the test chamber 38, and heat filament, respectively. The infrared sensor is positioned under the swipe and acts as a proximity sensor to detect the presence or absence of a swipe by the amount of light reflected back. The processor 200 or controller actuates the motor to drive a solution delivery manifold to the center of the swipe and in close proximity to the swipe to dispense the solution without dripping, regardless orientation. The controller can monitor fluid levels within each reservoir contained in the disposable cartridge. This is done by decrementing available volume each time the pump is actuated and when the count reaches a low threshold, the controller can indicate that the reservoir is out of chemical.

The system is powered by a 12-volt DC source, which can be generated from an AC/DC converter, a car outlet or from eight 1.5-volt batteries in series. The highest prioritized energy source is from an AC/DC converter followed by the one from a car outlet, then the energy from batteries. The 12-volt DC power source will supply current to the heater and the piezoelectric unit or pump. It is also connected to the low drop voltage regulator to generate different voltage levels such as 5 V, 2.8 V and 3.3 V, which are necessary for the processor and for other peripherals as well.

One example of the of a sequence involving chemistry time, temperature ramp rates and hold times to optimize each of the results for explosives, drugs, or other threat chemicals within a chemical reaction sequence. The system always adjusts the start temperature prior to running a particular sequence to a predetermined temperature value. An example of the predetermined temperature may be 35° C. whereby the swipe retaining a wet or dry sample is adequately held and in intimate contact with the elements of the swipe holder. Not mentioned in this section are the specific parameter controls for fan speed, LED lighting, piezoelectric or pumping increments, GUI, camera, speaker, or display.

The following is an example process to test for an explosive. The background image of the swipe at a particular temperature is taken so as to subtract out any colors that may be present on the swipe prior to analysis. A selected chemical reactant from one of the reservoirs is then applied onto the swipe in a non-drip fashion and in a volume of 20-30 µL, most favorable being 25 µL. The system takes second image of the chemically reacted sample on the swipe and immediately processes this image from subtracted background for color indicating peroxides. The second image then becomes the new background image whether peroxides are present or not for the next analyte sought (hexamethylene triperoxide diamine HMTD).

Further reacting sample material on the swipe, the heater element begins rapidly heating only the sample area on the swipe with temperature setting ramp rates of 10-20° C. per minute to 115° C., most favorable being 15° C. per minute. During the ramp, a third image is taken between 5-15 seconds, 12 seconds being most favorable, to analyze for color indicating HMTD. The system takes third image of the chemically reacted sample on the swipe and immediately processes this image from second background for presence of HMTD. Once the heater element reaches 115° C., it then holds for 20-40 seconds, 30 seconds being most favorable. The third image then becomes the new background image whether HMTD was present or not for the next analyte sought (triacetone triperoxide TATP).

During the hold time, a fourth image is taken of the chemically reacted sample on the swipe at 25 to 30 seconds, 28 seconds being most favorable, and immediately processes this image from third background for presence of the color indicating TATP. The fourth image then becomes the new background image whether TATP was present or not for the next analyte sought (chlorates).

During the same hold time, a fifth image is taken of the chemically reacted sample on the swipe at 25 to 35 seconds, 30 seconds being most favorable, and immediately processes this image from fourth background for presence of the color indicating chlorates. The fifth image then becomes the new background image whether chlorates were present or not for the next analyte sought (TNT).

The heater element begins rapidly heating only the sample area on the swipe with temperature setting ramp rates of 10-20° C. per minute to 140° C., most favorable being 15° C. per minute. Simultaneously, a second selected chemical reactant from one of the reservoirs is then pumped onto the swipe in a non-drip fashion and in a volume of 20-30 µL, most favorable being 25 µL. Once the heater element reaches 140° C., it then holds for 10-20 seconds, 10 seconds being most favorable. During the second temperature ramp, a sixth image is taken between 5-15 seconds, 8 seconds being most favorable, to analyze for color indicating TNT. The sixth image then becomes the new background image whether TNT was present or not for the next analytes sought all (high explosives).

The heater element begins rapidly heating only the sample area on the swipe with temperature setting ramp rates of 10-20° C. per minute to 155° C., most favorable being 15° C. per minute. Simultaneously, a third selected chemical reactant from one of the reservoirs is then applied onto the swipe in a non-drip fashion and in a volume of 20-30 µL, most favorable being 25 µL. Once the heater element reaches 155° C., it then holds for 10-20 seconds, 20 seconds being most favorable. During the third temperature ramp, a seventh image is taken between 5-15 seconds, 5 seconds being most favorable, to analyze for colors indicating all high explosives. The seventh image then becomes the new background image whether high explosives were present or not for the next analytes sought (all nitrates).

The heater element continues to hold at 155° C. and from 10-20 seconds, an eighth image is taken between 10-20 seconds, 15 seconds being most favorable, to analyze for colors indicating all nitrates. The heater element immediately cools down for the next sample run.

Another example of a single test involving chemistry time, and temperature settings and hold times to optimize results for a chemical reaction involves depositing one or more of the chemical reactants from their respective reservoirs onto the swipe in a non-drip fashion. This is to impart a single spot test or multiple spot tests for a single drug or drugs, a single explosive or explosives, or other threat chemicals at ambient or preset temperature conditions that results in a single color or an array of colors unique to that material under the temperature settings and reagents applied.

In one embodiment as a Portable Explosive Trace Detector (PETD), the system of FIG. 6 significantly enhances the detection of the explosive materials as well as speeding up the screening and detecting procedures at security checkpoints. First, the PETD automatically applies a series of chemical solution agents into the swiped sample and heats up to specific temperature to accelerate the chemical reactions. Second, an internal CMOS camera captures the chemical reaction images at its highest resolution, raw data for better image analysis. Third it then sends these raw images data to the LCD (Liquid Crystal Display) screen for the purpose of observation. Moreover, the JPEG codec is capable storing and replaying image functions. The LCD screen provides a high quality image for human viewing. In another embodiment, in place of JPEG, a bitmap image or an MPEG video or any suitable imaging storage format can be used. The LCD can analyze the image to identify explosive materials based on the provided chemical reaction database. Last but not least, the PC interfaces can be used to update software and firmware as well as to backup the data.

In one implementation, to start the analysis process, the system turns the piezoelectric units or micro-pump(s) N (i.e., N=1, 2, 3 . . . or a combination thereof) to disperse the chemical solution onto the swiped sample. The dispensing rate is set to 2 Hz. After dispersing chemical solution, the system starts heating the sample to excite the chemical reactions under controlled vapor, time, temperature, and chemical volume conditions specific to a particular analyte or group of analytes. A current of about one ampere is applied to heat up the heating filament. During the heating process, the fluctuation of the temperature is controlled by a feedback circuit with a thermistor.

When the temperature of the sample swipe reaches a predefined value, the system turns the heater off, the white light LED on and the fan on. The speed of the fan is adjustable using pulse width modulation control in one embodiment.

Before commanding the camera's CMOS image sensor to capture an image, the system waits for the chemical reaction to complete for around 1 ms. The captured image is then displayed on the LCD.

The system creates a result image by subtracting the captured image from the background one. Then the result image is compared with the color patterns in the lookup table stored in the system. If the results image matches some color pattern, the result probability will be displayed and an optional audible alarm is given or not. Otherwise, an appropriate message is displayed on the LCD.

During the process of writing to the memory, (e.g., saving results or updating database), the system is able to detect the memory capacity and give the user a warning of full memory. In such a case, the user needs to clear the memory by deleting certain files before commanding the system to continue its work.

In one embodiment, the system executes a prime piezoelectric or pump procedure to clear up air and chemical bubbles in the tubes of minimized length and diameter once the system has been idled for more than 12 hours. If the system has not been used for the past 12 hours then the system prompts the user to place an empty swipe sample into a clamp holder. Once a swipe sample is secured on the clamp holder, the system prompts user to do the prime piezoelectric or pump procedure by pumping chemical solutions onto swipe sample. During the prime piezoelectric units or pumps, the camera captures the image from the swipe and displays it on the LCD screen. During the prime piezoelectric units or pumps, no heat is applied to the swipe.

In one embodiment, in the main menu, user can see the date, the time and current status of the system. The system can generate a warning alarm once battery, chemical level and memory reach their minimal levels. The menu also contains three (3) software programmable buttons, namely New Analysis, Previous Results, and Settings. User can interact with these soft buttons by using the five hard buttons. The New Analysis option is highlighted as default. The usage of these soft buttons is as follows:

New Analysis: allows user to perform a new test.
Previous Results: allows user to trace back the data tested in the past.
Settings: allows user to set parameters such as date, time, to test the system reliability, or to connect to PC for firmware and/or database update.

The user can see the images taken by the camera. The system status is also displayed. In addition, three (3) soft buttons (Start, Stop, and Status) are provided. The Start option is highlighted as default.

Figure 7:
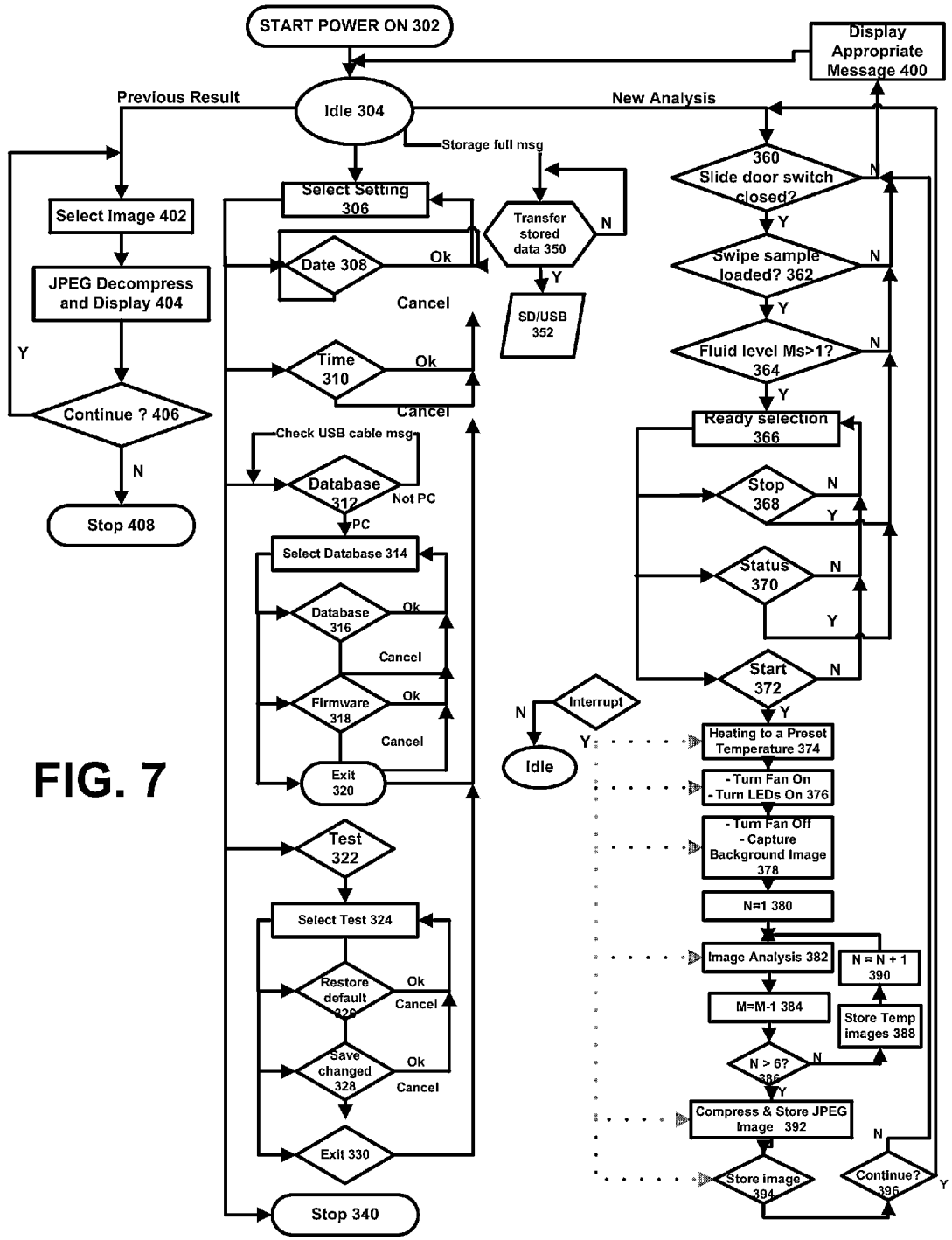
FIG. 7 shows an exemplary operational flow chart executed by the system of FIG. 2A.

FIG. 7 shows an exemplary operational flow chart executed by the system of FIG. 2A. When the system is turned on by pressing the Start Power On button, it will stay in IDLE state 304. In this state, the system waits for user commands. By default, both the camera lighting LEDs and the fan are turned off to save power. The system sends an appropriate message alarm to operator once chemical, battery, and memory reach their minimal level. User may command the system to perform a new test by selecting New Analysis, to view previous results and images by selecting Previous Results, or to update the firmware and/or database.

When the option of performing a new test is selected, the system checks whether the Slide Door Switch closed or not (360) via an infrared sensor (362). If the door is not closed, it will display a warning message (400) and return to IDLE state 304. Otherwise, it looks for a loaded swiped sample using the infrared sensor (362). The presence of the sample allows the system to move to the next state, where it checks for the fluid levels of the three reservoirs to ensure that the fluids are enough for the entire test process (364). The amount of fluid is determined by the number of dispensing (i.e., a full bottle is enough for a predetermined number of dispenses and the number is decremented during each dispensing).

Before continuing, the system checks the temperature of the filament if it is equal to 35° C. in one embodiment. Otherwise, it will have to heat the filament until the temperature of the filament reaches 35° C. (374). At this temperature, the user is allowed to choose different options. If the user presses the Stop button (368), the system will stop the work and return to the IDLE state. If the user chooses the Status button (370), the system will temporarily display its current task to turn the system status on/off. After that it returns and continues the previous work. When the user presses Start button (372), the system turns the Fan on to blow the fog or vapor away from the camera, turns the LEDs on, turns the fan 39 to a low speed and takes a background image using the camera (378). Then, the system will select a particular piezoelectric unit or micro-pump N=1 or a series of piezoelectric units or micro-pumps (N=1, 2. 3 . . . or a combination thereof) and start analyzing the sample based on the image analysis process (380-386). Once the New Analysis operation is in process, it takes a number of different tests (in one embodiment seven tests) non-stop and summarizes the test results after the last test has completed. The image results are saved automatically as a group by a time date stamp and can be further sorted by positive or negative results for ease of viewing recall (392-394). Different audible sounds can be played at the end of each test to catch the operator's attention. The image result is obtained by subtracting the current image from its initial background image. After finishing this analysis, the system asks user if he/she wants to review the test summary or else return to the main menu.

When the option of viewing previous results is selected, the user can select his/her desired filename and presses Display button to command the system to decompress and display the image and/or other necessary information (402-408).

When the option of updating date, time, database and/or firmware is selected (306), the system shows a menu to allow the user to choose different options such as update date, time, or upgrade the firmware, or test the reliability of the system. For example, when the user presses the date button (308), the system allows the user to change the date via the buttons of the system. After the date is confirmed to be changed, the system will store the change in its memory and return to the previous menu to allow the user to choose other options. The change of the time functions in the same manner as the change of the date (310).

In case the user wants to update the database by pressing Database button (316), the system communicates with the PC in order to set up a channel for data transfer (312). Upon a successful connection the user can update database and/or firmware. After the firmware or database is updated, the user presses the Ok button to return to the main menu. When the system connects to the PC unsuccessfully, it warns the user to check the connection (316).

When the user wants to test the reliability of the system, the user can press the Test button (322). As soon as this button is pressed, the user can test different system parameters. He/she can save the changed parameter or restore default parameter. When the user presses Exit button, system returns to the main menu.

By having all components under program control and by arranging for a known input to the system such as a controlled injection of target material, the system can perform self-calibration and self-diagnostic. The function of this program is to calibrate the entire system and determine and store the required time, and temperature parameter, among others. If these parameters are not within specified limits for any reason, the program can alert the user. Guided by a service program the user response can range from immediate shutdown to scheduling service at a later date, to simply noting the circumstances.

Figure 8:
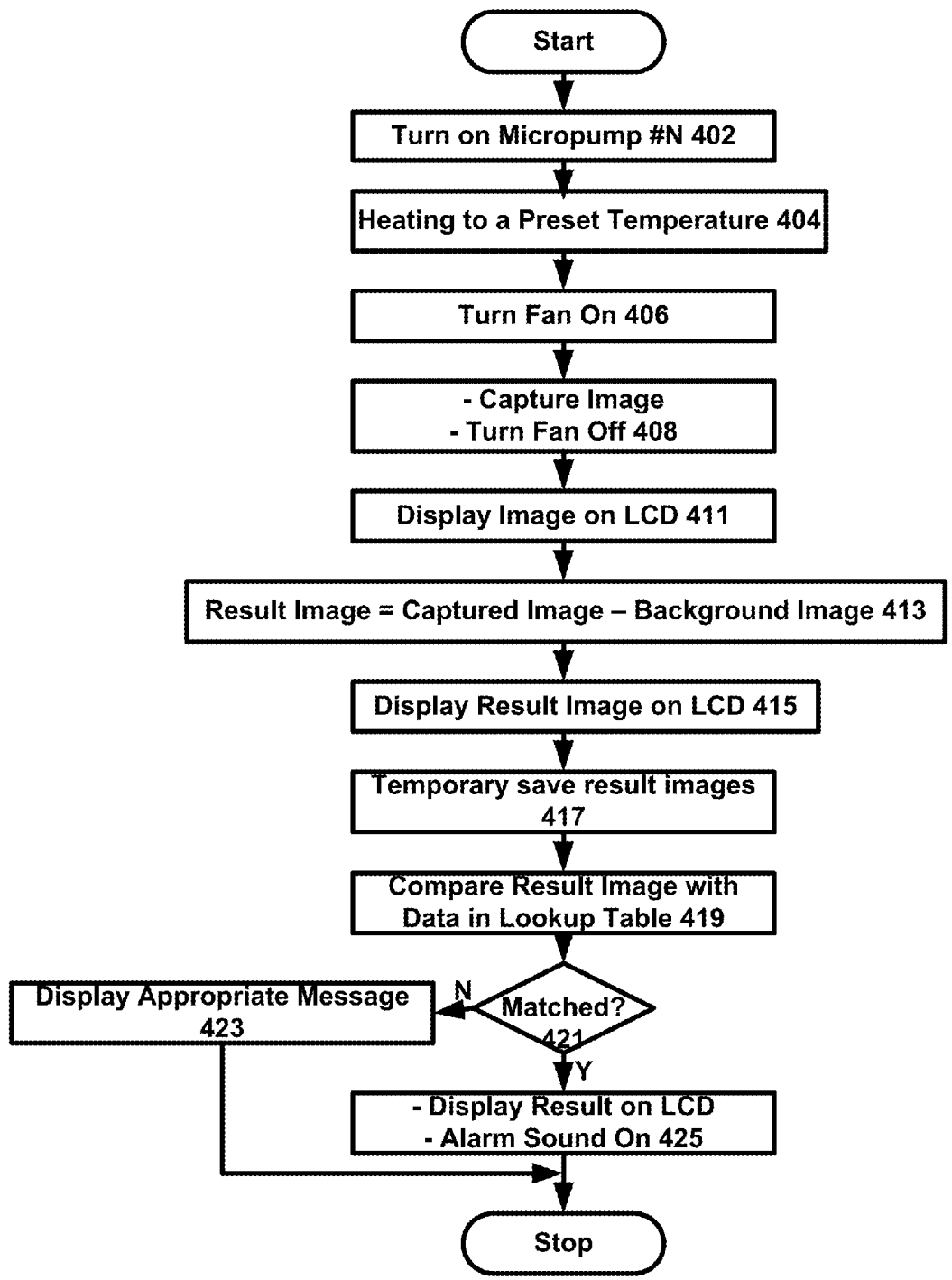
FIG. 8 shows an exemplary image analysis process executed by the processor of FIG. 6 to detect chemical agents automatically.

FIG. 8 shows an exemplary image analysis process executed by the real-time embedded system processor 200 to detect chemical agents automatically. To start the analysis process, the system turns the piezoelectric unit(s) or micropump(s) N (i.e., N=1, 2, 3 . . . or a combination thereof) to disperse the chemical solution into the swiped sample. The dispensing rate is set to 0.250 Hz. After dispersing chemical solution, the system starts heating the sample to excite the chemical reactions. A current of about 1 Ampere is required to heat up the heater filament. When the temperature of the sample reaches a predefined value, the system turns the heater off, the LED and the fan on. In one embodiment, before commanding the CMOS image sensor to capture an image, the system waits for the chemical reaction under optimized: time, temperature, volume dispensed, and vapor to complete for around 1 millisec. The captured image is then displayed on the LCD. The system creates a result image by subtracting the captured image from the background one. Then the result image is compared with the color patterns in the lookup table stored in the memory. If the results image matches some pattern, the result will be displayed and an audible alarm is given. Otherwise, an appropriate message is displayed on the LCD.

Due to the automated, reproducible analysis, the system provides an objective indication of potential threats with more accurate, un-biased results at night, high humidity, or bad weather conditions, and therefore, more convenient.

The invention may be implemented in hardware, firmware or software, or a combination of the three. Preferably the invention is implemented in a computer program executed on a programmable computer having a processor, a data storage system, volatile and non-volatile memory and/or storage elements, at least one input device and at least one output device.

By way of example, a block diagram of a computer to support the system is discussed next. The computer preferably includes a processor, random access memory (RAM), a program memory (preferably a writable read-only memory (ROM) such as a flash ROM) and an input/output (I/O) controller coupled by a CPU bus. The computer may optionally include a hard drive controller which is coupled to a hard disk and CPU bus. Hard disk may be used for storing application programs, such as the present invention, and data. Alternatively, application programs may be stored in RAM or ROM. I/O controller is coupled by means of an I/O bus to an I/O interface. I/O interface receives and transmits data in analog or digital form over communication links such as a serial link, local area network, wireless link, and parallel link. Optionally, a display, a keyboard and a pointing device (mouse) may also be connected to I/O bus. Alternatively, separate connections (separate buses) may be used for I/O interface, display, keyboard and pointing device. Programmable processing system may be preprogrammed or it may be programmed (and reprogrammed) by downloading a program from another source (e.g., a floppy disk, CD-ROM, or another computer).

Each computer program is tangibly stored in a machine-readable, removable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

The invention has been described herein in considerable detail in order to comply with the patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

What is claimed is:

1. A method to detect the presence of a substance on a test swipe, comprising:
    capturing a background image of the test swipe;
    applying one or more test chemicals to a test swipe to form sequences of color bar codes based on changing multiple sets of color bar codes generated for unique chemical reaction sequence for the substance;
    adjusting the temperature of the test swipe to a predetermined temperature range and hold times to during automated chemical deposition to provide chemical reactions to form new color bar codes for the substance;
    controlling a variable speed fan to avoid fogging the camera's lens;
    capturing multiple in-situ images of the test swipe after the application of chemical at the predetermined temperature range;
    subtracting the background image from the in-situ images;
    generating a difference value from any two images; and
    searching a known database to identify the substance based on changing multiple sets of color bar codes generated for unique chemical reaction sequence under specific time and temperature control.

2. The method of claim 1, comprising removing chemical vapor rising above a predetermined distance above the test swipe to avoid fogging the camera's lens.

3. The method of claim 1, comprising fanning chemical vapor rising above a predetermined distance above the test swipe to avoid fogging the camera's lens.

4. The method of claim 1, comprising allowing chemical vapor to remain within a predetermined distance above the test swipe.

5. The method of claim 1, comprising placing a solid state light source near the camera to provide uniform lighting at variable RGB settings and luminosity.

6. The method of claim 1, wherein the solid state light source comprises LEDs.

7. The method of claim 1, wherein the chemicals are applied in parallel on different parts of the test swipe.

8. The method of claim 1, wherein the one or more chemicals are applied in sequence, each swipe elevated to a predetermined temperature for each chemical.

9. The method of claim 1, wherein the chemicals are applied at one time.

10. The method of claim 1, wherein the chemicals are applied in sequence.

11. The method of claim 1, comprising generating a database of known substances by applying one or more chemicals to one or more control swipes.

12. The method of claim 11, comprising generating a signature of each substance by subtracting a background image against an image of each control swipe with one or more chemicals applied thereto, wherein the one or more chemicals applied to the test swipe and the control swipe are identical.

13. The method of claim 11, comprising exposing the control swipe and the test swipe to the same predetermined temperature sequence.

14. The method of claim 11, comprising dispensing one or more chemicals onto the test swipe and the control swipe through one or more pumps throughout the temperature sequence.

15. The method of claim 1, comprising removing chemical vapors after rising a predetermined distance from the test swipe but leaving vapors immediately in contact with the swipe.

16. The method of claim 1, comprising heating the test swipe to one or more predetermined temperatures and hold times using an automatic ramped heating feedback control.

17. The method of claim 1, comprising performing image analysis in real-time.

18. The method of claim 1, comprising protecting a camera with anti-fog protection.

19. The method of claim 1, comprising displaying the in-situ images in real-time for user review while analyzing the image to detect the substance.

20. The method of claim 15, comprising performing automatic calibration under different lighting environments.

21. An apparatus to analyze a test swipe to identify a chemical composition, comprising:
   a heater to warm the test swipe to various predetermined temperatures at various hold times;
   a clamp to secure the test swipe to the heater;
   one or more pumps to dispense one or more chemicals onto the test swipe from a disposable cartridge;
   a variable speed fan to remove chemical vapors rising a predetermined distance from the test swipe but leaving vapors immediately in contact with the swipe;
   a camera to capture an image of the test swipe for analysis and for real-time viewing by the operator to provide secondary level of assessment; and
   a processor and computer readable code coupled to the camera, the computer readable code includes capturing a background image of the test swipe; applying one or more test chemicals to a test swipe to form a color bar code based on changing multiple sets of color bar codes generated for unique chemical reaction sequence for the substance; adjusting the temperature of the test swipe to a predetermined temperature range; capturing an in-situ image of the test swipe after the application of chemical at the predetermined temperature range and hold times to during automated chemical deposition to provide chemical reactions to form new color bar codes for the substance; subtracting the background image from the in-situ image; generating a difference value from the two images; and searching a known database to identify the substance based on changing multiple sets of color bar codes generated for unique chemical reaction sequence under specific time and temperature control.

* * * * *